United States Patent [19]

Charvin

[11] Patent Number: 5,123,422
[45] Date of Patent: Jun. 23, 1992

[54] ELECTRODE-CARRIER DEVICES ABLE TO BE IMPLANTED IN THE COCHLEA SO AS TO ELECTRICALLY STIMULATE THE NERVUS ACUSTICUS

[75] Inventor: Guy Charvin, Antibes, France

[73] Assignee: Societe Anonyme MXM, Antibes, France

[21] Appl. No.: 538,200

[22] Filed: Jun. 14, 1990

Related U.S. Application Data

[63] Continuation-in-part of Ser. No. 329,888, Mar. 28, 1989, abandoned.

[30] Foreign Application Priority Data

Apr. 8, 1988 [FR] France ................... 88 04854

[51] Int. Cl.$^5$ .............................................. A61N 1/05
[52] U.S. Cl. ................... 128/784; 128/420.6
[58] Field of Search ............... 128/784, 786, 420.5, 128/420.6, 642

[56] References Cited

U.S. PATENT DOCUMENTS

| | | | |
|---|---|---|---|
| 4,284,085 | 8/1981 | Hansen et al. | 128/784 |
| 4,686,765 | 8/1987 | Byers et al. | 128/420.6 X |
| 4,832,051 | 5/1989 | Jarvik et al. | 128/420.6 X |

FOREIGN PATENT DOCUMENTS

0007157 1/1980 European Pat. Off. ............ 128/784

Primary Examiner—Lee S. Cohen
Attorney, Agent, or Firm—Ladas & Parry

[57] ABSTRACT

An intra-cochlea electrode carrier for implantation into a helically shaped tympanic canal has a plurality of segments. Each segment has opposite first and second surfaces, the first surface defining a length between opposite ends of the segment and a width between opposite sides of the segment, a height in cross section to the width being defined between the opposite first and second surfaces of the segment. Respective electrodes are on the first surfaces of the segments. Hinges on the opposite ends of the segments connect one end of each segment to one end of another segment, whereby to connect the segments into an elongated electrode carrier, the hinges having sufficient heights relative to the widths of the first surfaces of the segments and providing sufficient spacing between the ends of the connected segments for the electrode carrier to follow a helix of a helically shaped tympanic canal when implanted therein with the electrodes on the first surfaces of the connected segments oriented toward a nerve-receptor surface of the tympanic canal. A connector connects the electrodes of the connected segments.

10 Claims, 6 Drawing Sheets

ELECTRODE-CARRIER DEVICES ABLE TO BE IMPLANTED IN THE COCHLEA SO AS TO ELECTRICALLY STIMULATE THE NERVUS ACUSTICUS

This is a continuation-in-part of application Ser. No. 07/329,888, filed Mar. 28, 1989, now abandoned.

FIELD OF THE INVENTION

The object of this invention is to provide electrode-carrier devices able to be implanted in the cochlea, more particularly in the cochlea of a human being, so as to stimulate the nervus acusticus via electric signals supplied by an electronic auditive prosthesis device.

BACKGROUND OF THE INVENTION

The technical part of the invention concerns the construction of electronic auditory prosthesis devices.

There currently exist a number of electronic auditory devices for rectifying acute deafness. The comprise electrodes implanted in the cochlea, said electrodes being intended to transmit electric signals to the nervus acusticus fibers inside the cochlea.

Briefly, the acoustic waves are firstly transmitted by the ear-drum and ossicles to the liquid of the inner ear which in turn excites the ciliated sensorial cells of the cochlea.

In people suffering from acute deafness, the ciliated sensorial cells are deficient and the usual auditory prostheses, which have the effect of increasing acoustic energy, are ineffective.

For about twenty years, it has been possible to correct extreme deafness by using auditive protheses, known as bionic ears. These comprise an external device equipped with a microphone which captures sounds and with electronic circuits which break down these sounds into electric signals of different frequencies, and secondly electrodes which are connected to said electronic circuits either directly or by induction through the skin, and which are placed on an electrode carrier implanted inside the cochlea during a surgical operation.

The patent application FR.A. 2,383,657 (BERTIN & Co et al.) describes an auditory prothesis electronic device comprising an external transmitter which is in-duction-connected to a receptor implant comprising an intracochlear electrode carrier.

SUMMARY OF THE INVENTION

The object of this invention is an electrode carrier device which can be used with an external transmitter of the type described in the previous patent or with any other similar external transmitter.

Numerous types of electrode carrier devices are known which are thus called intra-cochlear devices and to which the manufacturers have given shapes, characteristics of embodiment, electrode implantation and composition characteristics, which are quite different from one device to another, this in order either to make the prosthesis as easy as possible for the surgeon to implant, and this without damaging the tissue of the cochlea, or to transmit the signals on the electrode as efficiently as possible.

It ought to be mentioned that the cochlea generally has the shape of a conical tube, having a length of about 35 mm which is housed inside a snail-shaped bony canal comprising two and a half spires. In cross section, the tube is divided into three canals which are filled with liquids. These canals are respectively denoted as: tympanic canal, vestibular canal and the cochlear canal. The cochlear canal is separated from the tympanic canal by the propria which contains the ciliated sensorial cells. The nervus acusticus or nervus cochleae penetrates into the cochlea along the snail axis by its base and comprises ramifications which are the spiral ganglia and which join up with the propria by following the inner face of the tympanic canal; therefore, the object of the electrodes of the prosthesis is to stimulate the end zone of said ganglia which extends as far as the propria. To this effect, the electrode carriers are generally placed in the tympanic canal.

The surgeon engages the end of the electrode carrier through the round window situated at the end of the tympanic canal and he pushes the electrode carrier in order to make it advance into the canal, this method requiring that the electrode carrier be sufficiently rigid so as to transmit the pushing pressure and sufficiently flexible so as to follow a helical canal for at least one revolution, and ideally for two. It is indeed essential that the electrode carrier extends over most of the length of the cochlea as the cochlea lengthwise comprises successive zones which are selectively excited by certain frequencies, which make it possible for the brain to recognize the sound frequencies.

Accordingly, to observe to a maximum the various aforesaid considerations, some of which appear in fact to be contradictory, many manufacturers and laboratories have studied various devices generally always giving preference to one consideration over another, some of which devices have been the subject of patent applications as follows:

The European patent application EP.Al. 183,605 (BERTIN & Co), describes electrode carrier devices intended to be implanted in the cochlea and which comprise a support made of an insulating biocompatible material in which holes are provided, all of which open onto a given support face and which each contain an electrode.

The patent application EP A3 0,007,157 (MELBOURNE UNIVERSITY) describes the electrode carriers intended to be implanted in the human cochlea and comprising a flexible tube around which are wound evenly spaced electrodes constituted, for example, by platinum sheets.

Another patent application EP A2 0,215,726 under priority of an Australian application of this same University and invented by Mr. G. CLARK describes an electrode carrier comprising near its end at least one discontinuity constituted by either a reduction of the section or by a material change affecting in both cases the entire section of the electrode carrier so as to facilitate deflection of the end when it encounters an obstacle while it is being implanted.

The patent application EP.A. 002.226 (Carl HANSEN) describes electrode carriers designed to be implanted inside the cochlea and which comprise a support made of an insulating material having the shape of a fork with two branches, each branch having a length corresponding to that of a spire of the cochlea into which said branch is introduced, each branch carrying several electrodes which are located on a given side of the branch.

The patent application EP.A. 0.002.068 (Carl HANSEN) describes electrode carriers designed to be implanted inside the cochlea and which comprise a flexible elongated support having the shape of a leaf, said support being pre-bent with a temporary longitudinal curve which roughly corresponds to the curve of the axis of the canal of the cochlea and is freed after having been placed inside the cochlea so as to revert to its actual bending state, which makes it possible to obtain optimum engagement between the nerve ends and the electrodes borne by the support, said electrodes being located along one of the support edges.

U.S. Pat. No. 4,686,765 (Charles L. BYERS) describes an intra-cochlear electrode carrier, whose configuration, even in inoperative condition before any intervention, has the shape of a spiral corresponding to the natural spiral shape of the cochlea; the electrode carrier is molded in a supple elastomer material and comprises two metal electrodes in chip-form, the chips being placed according to two virtually perpendicular directions, on the one hand, inwards of the spiral in the direction of the nervus acusticus and, on the other hand, towards the propria.

U.S. Pat. No. 4,832,051 (Robert K. Jarvik) describes an electrode carrier device having axial rigidity and lateral flexibility properties due to adjacent elements placed along the axis of the device, which elements are virtually incompressible in the direction of said axis and laterally flexible one with respect to the others, of helical spring type and carrying electrodes distributed along the spires of said spring. This patent also teaches another embodiment, still with the aim of easing up the penetration of the electrode carrier, which embodiment, on the other hand, is not claimed, due to the fact that it uses known implementation means and that it is difficult to carry into practice and in any case rather inefficient: this is a prosthesis of flattened rectangular cross-section with slits provided in at least part of the thickness and over two-thirds to three-quarters of the width of said section, so that the upper part of said slits corresponding to the width of the section where they are situated, is open and the lower part is compressed to form a curve which allows following of the cochlea curve, as in the case of a spring, the electrodes being situated at the upper part of said curve, namely towards the so-called external face of the cochlea which contains no nerve end.

The results obtained with the electrode carriers existing to-date such as those described in the afore-mentioned documents, are not always satisfactory, either as regards the intelligibility of the sounds perceived by the patient, or as regards their implantation by the surgeon.

Indeed the insertion of an electrode carrier inside the cochlea by pressing on the latter so that it follows and adopts the spiral shape of the cochlea, may result in the electrode carrier behaving like a burin which damages the membranes and even, in some cases, the terminations of the nervi acustici. This danger is emphasized in the four aforementioned patents EP. A2 0 215,726, U.S. Pat. No. 4,832,051, EP. A 002,226 and EP.A. 002,068 which seek to rectify this situation, either by creating a punctual discontinuity at the extremity by creating discontinuities all along the electrode carrier in order to have a continuous lateral flexibility, or by dividing the electrode carrier into two branches, each of these being inserted into a single spire of the cochlea, or by giving the electrode carrier a temporary prebending, which involves complex solutions and does not reach the target result, since instead of damaging the externally curved wall, there is a risk of damaging the inner wall which is however the most sensitive one, as in fact in U.S. Pat. No. 4,686,765.

Certain manufacturers of these intra-cochlear catheters, some of which are more rigid than others, because of their design, have effectively searched for devices comprising mechanical discontinuities in order to facilitate the insertion of the electrode-carrier into the cochlea. Most of these devices have in fact been widely known for a very long time in other medical applications. Indeed, the systems of mechanical discontinuities such as springs, slits, hinges, etc. . . . are widely used in cardio-vascular type catheters, flexible guides, cables for pacemaker electrodes, neuro-stimulation catheters, etc.

For example, certain electrode-carrying catheters such as those of the invention described in U.S. Pat. No. 4,832,051 use these known devices (springs, slits, . . . ) for the sole purpose of giving flexibility to the catheter, without seeking to orientate the electrodes. In particular, the electrode-carrying catheter described in a version of the JARVIK invention, presents slits whose geometry and position (inside the same plane) are such that the electrode carrier curls into the cochlea, thereby being in contradiction with the aim of the present invention.

Indeed, tests carried out on a cochlea model with electrode carriers conforming to those described in the document EP. Al. 183,605, this also being the case with electrode carriers in accordance with the patents EP. A2. 0,215,726 and for certain applications U.S. Pat. No. 4,832,051, have shown that, when this electrode carrier is inserted inside a cochlea, it inevitably tends to curl up in following the longitudinal curve of the cochlea with the result that the electrodes are oriented in all directions and even sometimes outwardly, as in the version of flat rectangular cross-section according to the U.S. Pat. No. 4,832,051 of JARVIK, instead of being directed towards the propria. As a result, the current lines derived from certain electrodes are not captured or very faintly captured by certain sensitive zones of the cochlea where sound distortion renders these sounds almost unintelligible.

The electrode carriers described in the patent EP 0,007,157 and in certain versions of U.S. Pat. No. 4,832,051 to correct the aforesaid effects, which use circular electrodes, do not have this drawback. However, circular electrodes create current lines which diverge in all directions, which means that the energy emitted by each electrode is dispersed and only one small part reaches the nerve ends.

The problem that the invention is seeking to solve is essentially that of procuring electrode carriers intended to be inserted into the tympanic canal of a cochlea through the end window thereof which improves the intelligibility of sounds by a good stimulation of the sensitive zones of the auditory system. Moreover, these electrode carriers must not injure either the tympanic canal of the cochlea, or and especially the propria and the inner wall.

To achieve this, it is necessary to obtain electrode carriers which have the qualities and characteristics of all the aforecited one, but without the disadvantages, i.e. first they must be sufficiently rigid so as to be able to be pushed in order to force them to move into the spires of the tympanic canal and yet be sufficiently flexible so as to adopt the helical shape thereof without damaging the walls of the canal or the nerve ends; second and more particularly, they must not be twisted around their longitudinal axis, so that the electrodes located all along the electrode carrier are placed towards the sensitive zones of the cochlea opposite the nerve ends and as close as possible to the latter.

The solution to the problem raised is an intracochlear electrode carrier device implantable in the tympanic canal, whose helical shape curls around an osseous axis corresponding also to that of the common section of the nervus acusticus so as to electrically stimulate the sensitive zones corresponding to the nerve ends of the latter: the device comprises a flexible support whose body is made of a biocompatible material shaped as an elongated rod in the direction of its axis, and has a substantially thick cross-section with respect to its width which can be laid substantially flat, when inoperative, in a reference plane, substantially parallel to its own axis, which rod further comprises mechanical discontinuities defining and separating sections hingedly joined one to the other and carrying at least one electrode connected via a conductor to a signal receiver generally provided under the skin at the back of the ear, or outside it, which discontinuities form hinges, whose rotation axes are substantially perpendicular to said reference plane and on the other hand, have sufficient rigidity so that rotation of the sections is performed substantially in parallel to said plane, and each of said electrodes is placed on a section, its active part being directed to face the solid angle, determined firstly by said reference plane, and secondly, by a plane substantially perpendicular to the first, and substantially parallel to the two rotation axes of said section with respect to the two sections adjacent thereto, so that when the electrode carrier is inserted in the cochlea, the flexible support follows spontaneously the curvature of the tympanic canal by rotation of the sections about their said rotation axis, which remain substantially parallel to the winding axis of the cochlea, and which inevitably self-orientate the surface of the active part of the electrodes oriented towards the same substantially nerveless zone to be stimulated, either towards the propria, or towards the spiral ganglia, or towards both.

According to a preferred embodiment, said mechanical discontinuities are transversal slits perpendicular to the flexible support's own axis and which extend substantially over an important part, i.e. at least half the width, and preferably three-quarter, of the cross-sections thereof situated between two sections, so that the non-slit part of the latter is continuous and constitutes said hinges. Advantageously, said slits are situated in each interval between two successive electrodes.

Advantageously, said surfaces of the active parts of the electrodes are visible on the surface of said body, and are oriented towards the two sides of said solid angle, so that once they are introduced in the cochlea, they can stimulate both the propria and the inner face of the tympanic canal behind which the spiral ganglia are situated.

According to an embodiment, said mechanical discontinuities are veritable hinges with permanent contact points, whose articulation axes are the said rotation axes, and which interconnect independent sections one to the other, which hinges are preferably constituted on a section on one side of a cylindrical male part engageable on the other side in a female part corresponding to the adjacent section.

According to another embodiment, said electrodes have a continuous active surface which adopts the contours of said body along two sides thereof corresponding to those of said solid angle in facing relationship; said electrodes comprise a tail which is embedded in the body of said support and which is in the shape of a cross through which are threaded said conductors of connection with said electrodes.

The result of the invention is to provide new electrode carriers intended to be inserted inside the cochlea of a human being, especially inside a human cochlea, in order to stimulate the nervus acusticus by means of electric signals received from an external portable device which captures the sounds, converts them into electric signals and filters them so as to break them down into determined frequency bands which are each sent to one of the electrodes.

Owing to the division of these either into sections or segments joined by hinges constituted, for example, by transversal slits, one electrode according to the invention has a sufficient rigidity so as to be able to be pushed towards the front and is flexible so that it easily follows the curvature of the cochlea over about one and a half turns without risking damaging the membrane which delimits the tympanic canal in which it is inserted. Moreover, and simultaneously, and this is the main innovation and originality of the present invention, due both to the position of the rotation axis of the sections with respect to the active surfaces of the electrodes, and to the sufficient rigidity of the rotation axes, due, among other things, whenever slits are used, to the substantially and essentially thick shape of the flexible body, it is possible to insert the latter in the cochlea without curling it and without turning it around its longitudinal axis, so that it is possible to place the visible part of all the electrodes on the same side of the electrode carrier and of being certain that once the electrode carrier is placed inside the cochlea, all the visible parts of the electrodes, which are in contact with the liquid contained in the tympanic canal, are found to be spontaneously orientated towards the inside of the cochlea, namely towards the sensitive cells and/or the spiral ganglion of the nervus acusticus. This is not obtained in any of the devices described in said patents.

Accordingly, an electrode carrier according to the invention makes it possible to obtain good stimulation of the nerve cells from electric signals and improves the intelligibility of sounds received by the patient, which is the principal aim, in addition to the low risk of injury to the membrane.

BRIEF DESCRIPTION OF THE DRAWINGS

The following description refers to the appended drawings which represent, without being restrictive, embodiment examples of the electrode carrier according to the invention.

DETAILED DESCRIPTION OF PREFERRED EMBODIMENTS

Figure 1:
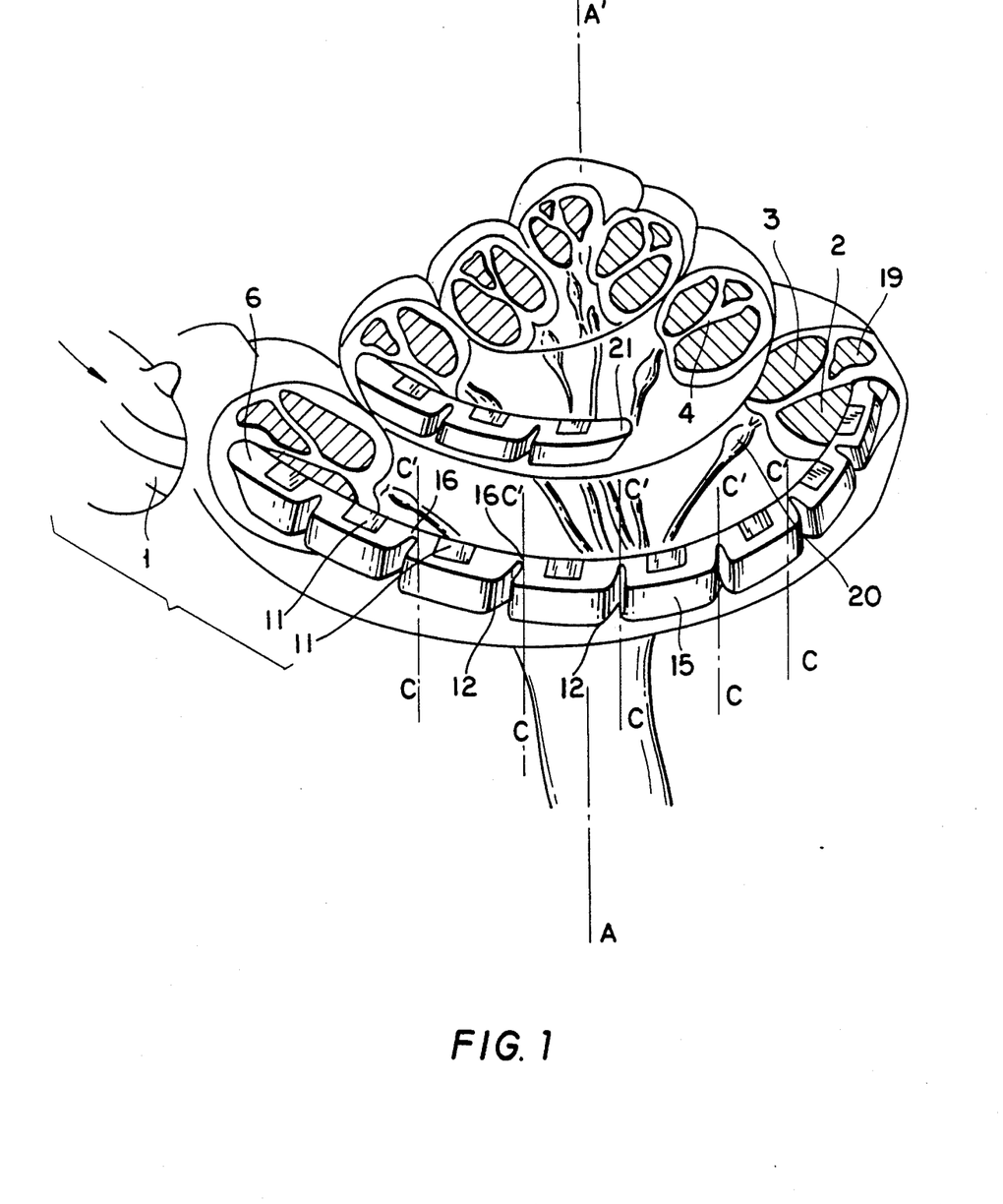
FIG. 1 is an enlarged, partly cut away, perspective view of a human cochlea in which is inserted an electrode carrier according to the invention.

FIG. 1 shows a human cochlea of a right ear. This has the shape of a helical or spiral canal formed inside the temporal bone 1 and winding around a conical bony axis known as the columella. This canal makes about two and a half revolutions or turns around the columella. It contains three canals delimited by membranes and filled with lymph: the tympanic canal 2 and the vestibular canal 3 which are separated from each other by a membrane 4 known as a propria, and the cochlea canal 19. The nervus acusticus comprises a common nerve vessel situated on the axis AA' and ramifications called spiral ganglia 20 whose ends are found towards the propria. These nerve ramifications and ends comprise ciliated sensorial cells and constitute the acoustic papilla, which normally captures the acoustic vibrations of the liquid contained in the two canals and converts them into nerve impulses which are transmitted to the brain.

The ciliated sensorial cells divided along the cochlea selectively capture the sound frequencies.

FIG. 1 shows an electrode carrier 6 inserted inside the tympanic canal 2.

The surgeon, having made an opening in the temporal bone 1, introduces the distal extremity of the electrode carrier into the round window situated at the extremity of the tympanic canal and then pushes in the electrode carrier which needs to advance towards the top of the cochlea by turning around the columella over a length of about 20 mm. The electrode carrier is lined with electrodes, for example twelve, distributed over the entire length.

If one looks at a cochlea from the bottom to the top, i.e. from A towards A', the cochlea of the right ear turns counterclockwise, whereas the cochlea of the left ear turns in clockwise direction.

Figure 2:
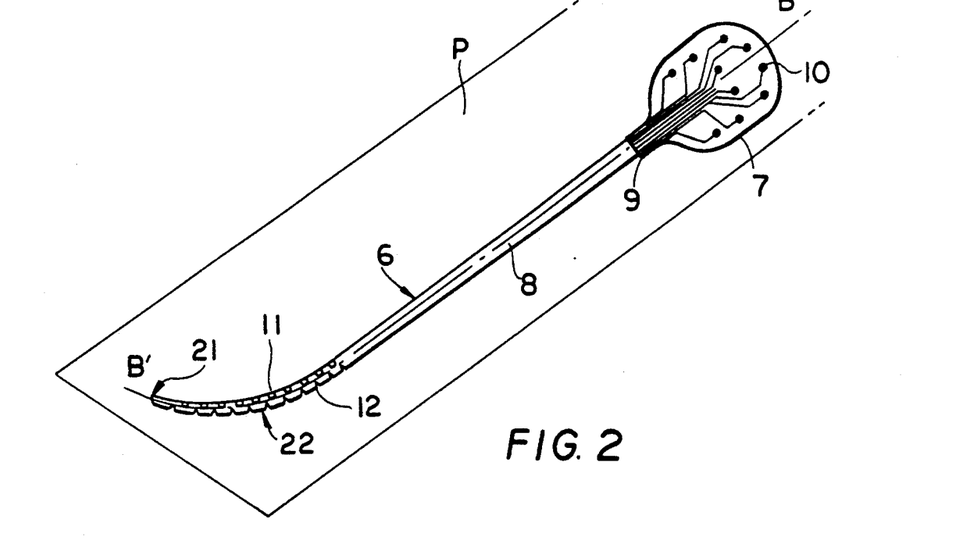
FIG. 2 is a view of the entire internal part of an auditive prosthesis comprising an electrode carrier according to the invention.

FIG. 2 represents an overall plan view of an electrode carrier device according to the invention such as it is before being implanted inside the cochlea: the device can thus be laid substantially flat, when inoperative inside a reference plane P, which in the present case is that of the figure and substantially parallel to that defined by its own axis BB'.

The device comprises a receiving head or receiver 7 which is placed under the skin behind the ear opposite an emitting head or electronic apparatus situated outside and which emits electric signals originating from a portable device carried by the patient and equipped with a microphone. The signals emitted by the emitting head are transmitted by induction to the receiver 7 which therefor has no source of energy.

The electrode carrier device according to FIG. 2 further comprises a support 8 whose body is made of a biocompatible insulating material, such as silicone, and has an elongated shape which follows its own axis BB'. Small conductive filaments 9 pass inside this body, said filaments being insulated from each other. Each filament has one end 10 situated inside the receiving head and connects the latter with a stimulation electrode 11 borne by the distal end 22 of the rod 8.

The electrodes 11 are distributed over one length of the rod distal end 22 which is about 2 cm from the point 21 thereof, this length corresponding to part of the length of a cochlea.

It should be mentioned that all cochleas individual have roughly the same dimensions and that a person's cochlea is formed from infancy and does not normally change dimensions through existence, therefore a single size of electrode carrier size may be used throughout the lifetime of any person.

FIG. 2 shows all the electrodes 11 disposed on a given side of the electrode carrier.

Figure 10:
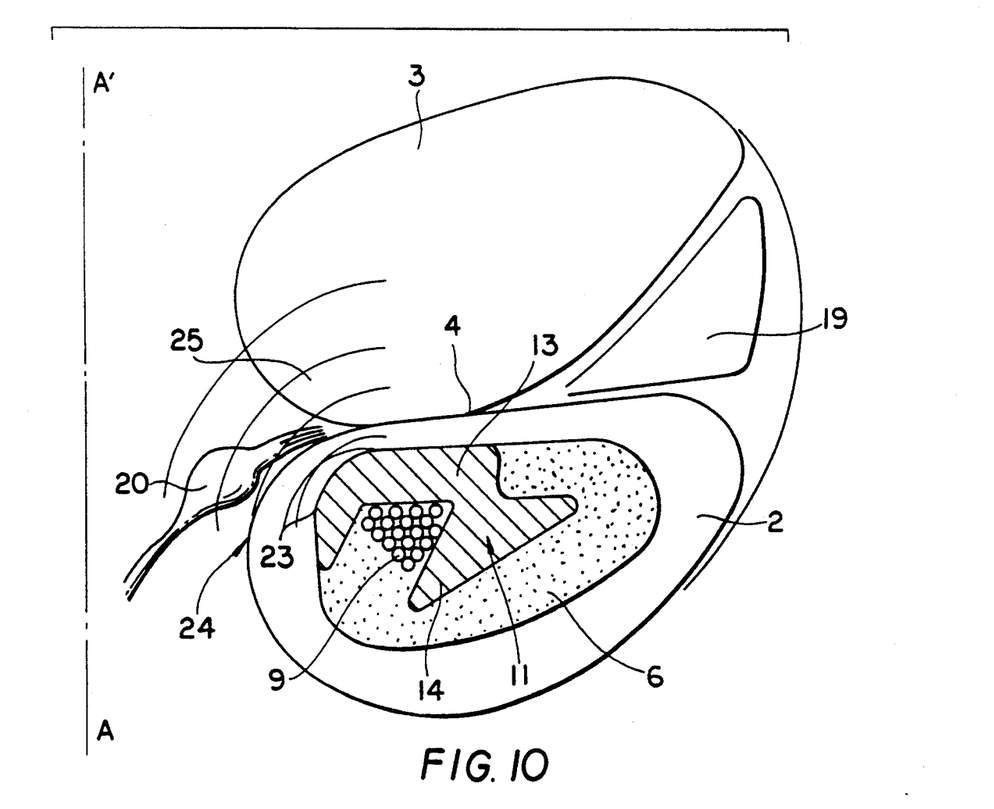
FIG. 10 is section of the cochlea according to FIG. 1 with an electrode carrier cut along XX of FIG. 8.

FIG. 1 and especially FIG. 10 show that the ramifications of the nervus acusticus 5 ending at the propria 4 are located on the inside of the cochlea towards the axis AA'.

To obtain the best possible transmission of the electric signals between the electrodes and the nerve ends, it is thus preferable that the electrodes be located opposite the sensitive internal zone of spires where the spiral ganglia 20 reach, and the propria 4.

In the case of an electrode carrier intended for a right ear whose cochlea turns counterclockwise, the electrodes 11 are placed on the left side of the body of the flexible support 8 when this is laid substantially flat in inoperative position in its reference plane P with the face which is supposed to be oriented, after insertion into the cochlea, towards the propria, being oriented upwardly and when looking at the base of the rod, towards the point 21 which penetrates first into the cochlea.

On the contrary, in the case of an electrode carrier designed to be inserted in the left ear which turns clockwise, the electrodes 11 are placed on the right of the body of the flexible support 8 of the electrode carrier when this is laid substantially flat in inoperative position in its reference plane P with the face which is supposed to be oriented after insertion into the cochlea, towards the propria, being oriented upwardly and when looking at the base of the rod towards the point 21 which will penetrate first into the cochlea. This disposition is illustrated in FIG. 2.

The problem to be solved is that of producing electrode carriers which retain their orientation when inserted into the cochlea so that the stimulation electrodes 11 all remain placed on the inside over the whole length of the electrode carrier.

Indeed, if a flexible rod having, for example, a conform and continuous circular section, is inserted into a sprial circuit, the internal fibers are compressed and the external fibers are tensioned and these internal stresses result in the rod twisting around its axis.

The problem raised is solved and illustrated in FIG. 1 by electrode carriers in which the distal part 22, which carriers the electrodes 11 and is engaged in the cochlea, is constituted by sections 15 interconnected by hinges 16 around each of which two successive sections can pivot with respect to each other according to an axis CC' substantially parallel to axis AA' of the cochlea.

An electrode carrier cut into joined successive sections has the advantage of transmitting thrusts so that it can be easily inserted inside the cochlea and, at the same time, of bending easily in order to take up the helical shape of the cochlea without twisting around its axis BB' and without any risk of the cochlea membranes being damaged.

FIG. 2 shows an embodiment in which the distal part comprises transversal slits 12 which extend over one part of the cross-section of the support and which are located on the side opposite the electrodes 11, namely on the external side in the figure illustrating the electrode carrier bent in a direction which is not necessarily its natural direction in inoperative position as this depends on the stiffness of the material, and on the dimensions and shape of the slits.

Figure 3:
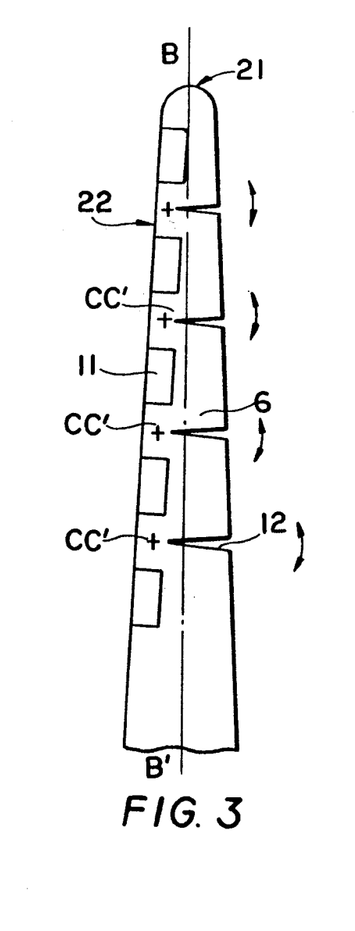
FIGS. 3 to 5 are plan views of several embodiments of electrode carriers intended for a right ear.

FIG. 3 shows on a larger scale a top view of the distal end of an electrode carrier intended to be inserted in a right ear, and laid in the same plane and in the same way as that described with respect to FIG. 1.

The body 6 made of a biocompatible material bears electrodes 11 made of biocompatible inert metal, such as platinum.

The electrodes 11 are located on the left side looking towards the point 21. The body 6 is divided into successive sections by slits 12 situated on the side opposite that carrying the electrodes 11 and between two electrodes, and which cut at least across half the width of body 6 and preferably up to three-quarters, since the object is to constitute veritable hinges around an axis of given direction and not just to give flexibility in any direction as in the other heretofore known designs.

Figure 4:
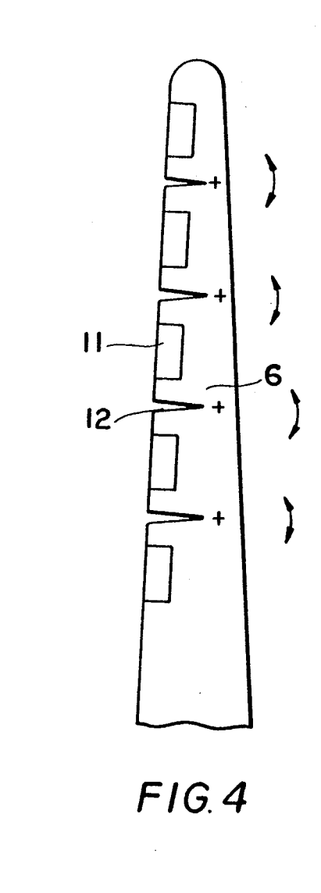

FIG. 4 shows a plan view, in the same conditions, of another embodiment of an electrode carrier also intended to be inserted in a right ear and in which the body 6 bears electrodes 11 and slits 12 pushed in between the electrodes on the same side as the latter.

Figure 5:
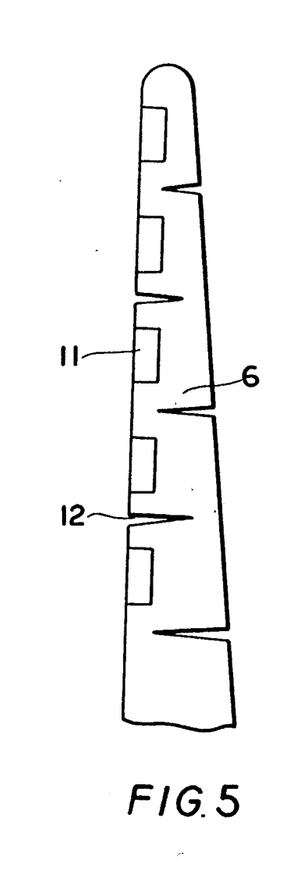

FIG. 5 shows a plan view, in the same conditions, of another embodiment of an electrode carrier also intended to be inserted in a right ear and in which the body 6 bears electrodes 11 situated on the left side looking towards the point and slits 12 situated on both sides.

The electrode carriers intended to be inserted into the left ear are symmetrical, that is the electrode 11 are situated on the right side looking towards the point in the same configuration.

When an electrode carrier according to any one of FIGS. 3 to 5 is inserted into a right ear cochlea, the body 6 bends and is wound counterclockwise and the slits 12 facilitate bending and ensure that the bending and/or compression stresses are not created in the external and/or internal fiber, which has the effect of ensuring that the body 6 does not curl up by pivoting around its longitudinal axis so that the electrodes 11 remain inside the curve opposite the already defined reference plane P and planes N normal thereto; namely on the side of the nervus acusticus ends and close to the latter: as illustrated in FIG. 1.

Figures 6, 7, 8:
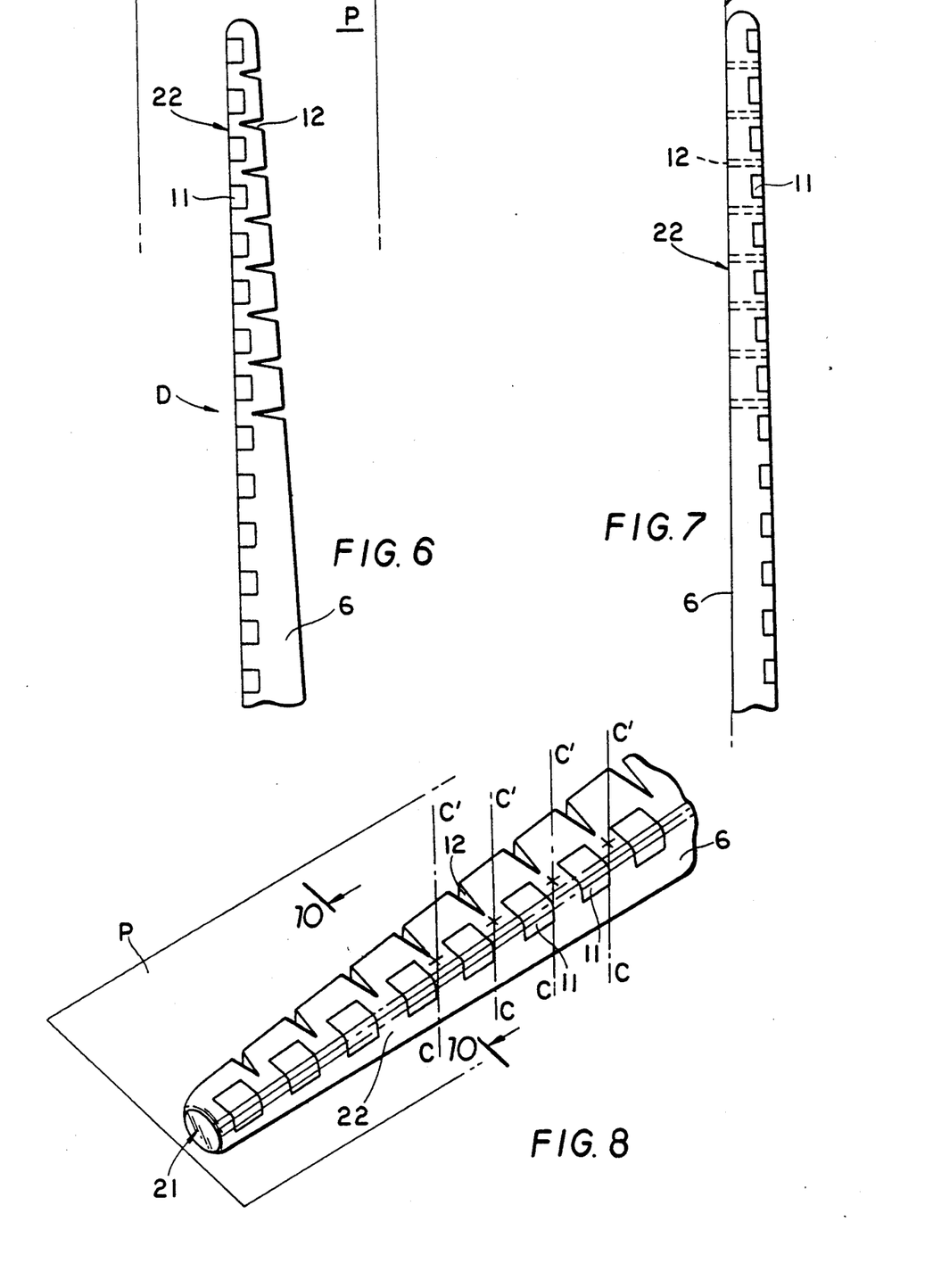
FIGS. 6 to 8 are respectively a plan view, an elevational view and a perspective view of an electrode carrier intended for a right ear.

FIGS. 6 and 7 respectively represent a plan view and a side view along axis D of FIG. 6 of the distal end 22 of an electrode carrier intended to be inserted into the cochlea of a right ear and laid substantially flat on its reference plane P, such as defined in the preceding figures.

The body 6 is preferably made of silicone. It bears fifteen electrodes 11 distributed along the left side looking towards the point. The distal part is divided into sections by eight slits 12 situated on the side opposite the electrodes and in the middle of the eight intervals situated between the nine end electrodes. The rear part, on the other hand, where the last six electrodes are situated and which occupies the rectilinear entrance of the cochlea, is not divided into sections.

FIG. 8 is a perspective view of the distal end 22 of an electrode carrier whose body 6 is laid inside already defined reference plane P and has a cross-section of general hemispherical shape with rounded angles.

The electrodes 11 are placed astride on the edge located on the upper left side looking towards the point 21. The slits 12 cut the lateral right face and are located in the middle of each interval between two electrodes.

Figure 9A:
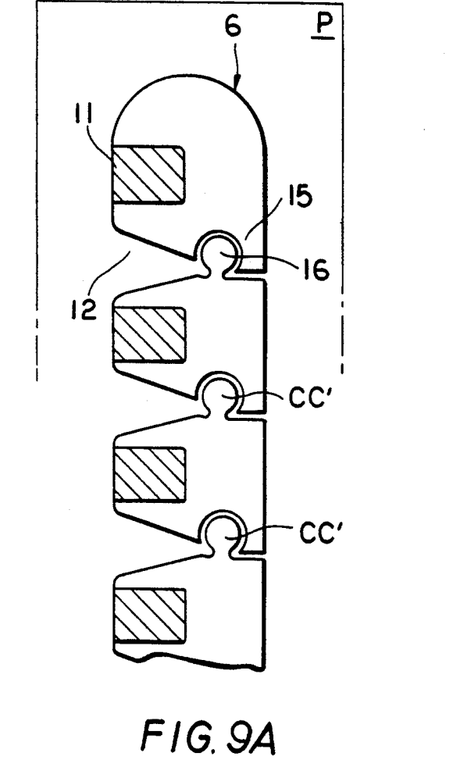
FIGS. 9A, 9B and 9c are plan views and perspective views of other embodiment examples of electrode carriers intended for right ears.
Figure 9B:
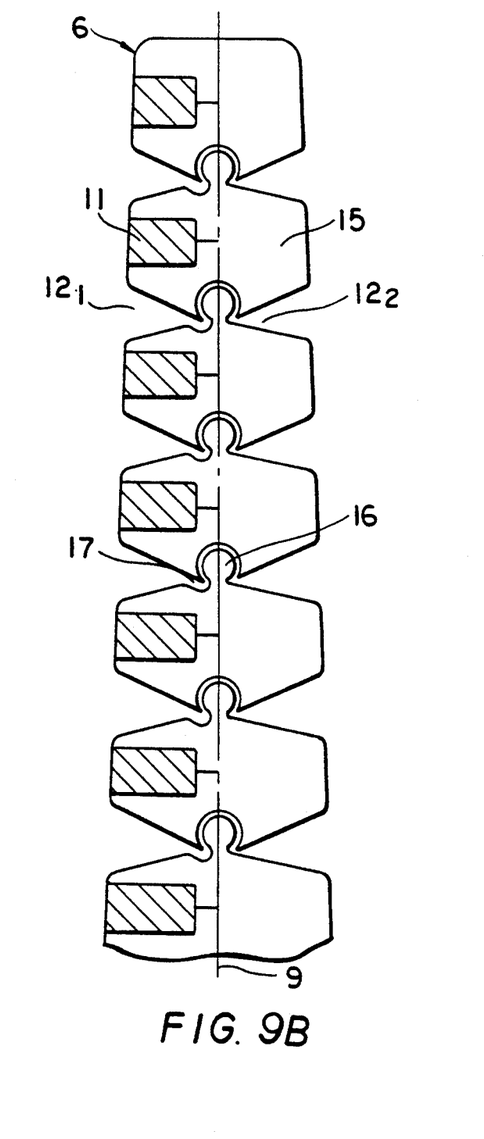

FIGS. 9A and 9B are plan views of two other examples of embodiment of an electrode carrier according to the invention again laid in their reference plane P and again intended for a right ear. The section 15 carrying the electrodes 11 are in this case independent of each other and are interconnected by real hinges 16 ensuring that they are joined in relation to each other and allowing their rotation inside a determined plane parallel to plane P and perpendicular to the axis CC' of these hinges and in a preferred direction, either for example, via an offsetting of their axis with respect to that of the body 6, as shown in FIG. 9A, or via an assymmetrical profile of the slits 12, as shown in FIG. 9B, thus constituting a standard preferential curvature bicycle chain type structure of preferential curvature.

In FIG. 9A, the slits 12 are located on one side onlyso as to allow for the bringing together of the sections 15 by pivoting towards this same side and on the other side the section elements take support one against the other when the body 6 is presented straight.

In FIG. 9B, the slits 12 are disposed on both sides of the hinges 16, but with a dissymmetrical profile 17 of the sections around the latter.

These hinges 16 are constituted, for example, by a cylindrical male part on one side, which can be embedded into a corresponding female part on the other side.

Figure 9C:
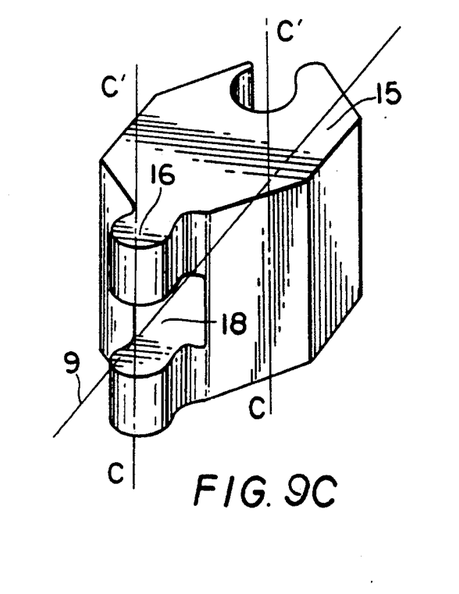

The wires 9 connecting the electrodes 11 then pass from one section 15 to the next, in several possible ways, such as for example: either they are disposed at the side of the hinges and pass backwards through said slits 12 with a slight excessive length to allow their extension movement; or they pass through the hinges 16 themselves whose male parts are then recessed, in order to allow their rotation due to the flexibility of the wires and of the material as shown in FIGS. 9B and 9C, or they are interrupted at the level of said hinges which then comprise rotary contacts in facing relationship, on each male and female parts, thus ensuring electric continuity irrespective of the angle of rotation.

FIG. 9C is a diagrammatic perspective view of a section 15 without its electrode and, as shown in FIGS. 9A and 9B, with a wire passage 9 in the plane of the fulcrum pin of the hinge 16. The male part of the latter is recessed in its middle so as to constitute the zone 18 for passing wires which then authorize, through their flexibility, the self-orientation of the electrode carrier.

FIG. 10 is a cross-section along XX' of an electrode carrier according to FIG. 8, placed in the cochlea according to FIG. 1.

This figure shows an electrode 11 which comprises a head 13 and a tail 14.

The external surface 23 of the contour of the head 13, which is visible, forms the active part of the electrode: in this example of embodiment, it is continuous and adopts the shape of one part of the contour along two sides of the body 6 corresponding to the upper face and to the left lateral face of said body which is constituted of an insulating support 6. The tail 14 is embedded in the mass of the body 6. It has the shape of a bent cross and the conductors 9, which electrically connect the electrodes to the receiving head 7, are housed inside the cross. One of the conductors is welded to each of the electrodes.

When an electrode carrier according to FIGS. 3 to 9 is inserted inside the tympanic canal 2 of the cochlea, the upper flat face of the active part 23 is placed in facing relationship and substantially parallel to the propria 4 and the lateral part is orientated to be substantially parallel to winding axis AA' of the cochlea, i.e. towards the internal face 24 of the tympanic canal immediately proximate to the spiral ganglion 20 and to the ends of the nervus acusticus, so that the signals emitted by the electrodes effectively stimulate the whole of the zone 25 where the nerve cells are situated.

In order to produce an electrode carrier according to the invention, the electrodes 13 and conductors 9 are preferably placed inside a mold into which the silicon is then poured. The slits 12 may be obtained by internal edges of the mold or even by transversally dividing up the body after taking it out of the mold.

In all the embodiments according to the invention as in the previously-described examples, the body 6 of the electrode carrier is divided into successive sections separated by discontinuities, such as open slits 12. These discontinuities, such as the slits and hinges as described in FIGS. 9, may be blocked up and covered with a biocompatible elastomer material sufficiently ductile and different from the material composing the body 6 so that the discontinuities of the mechanical properties are thus retained as described previously and make it possible to ensure self-orientation of the electrode carrier when the latter is inserted to the cochlea, while ensuring that this electrode bends easily and has a uniform external surface.

FIG. 10 represents a cross-section of a section of electrode carrier: the surface of this section reduces preferably from the base towards the point 21 as illustrated in the preceding figures, thereby following the sections along the profile of the cochlea which is also progressively decreasing.

According to one embodiment, all the sections of the body 6 of the flexible support which are progressively reducing from the base towards the point, which penetrate first into the cochlea and which are substantially thick with respect to their width, are approximately oval-shaped, with one end thicker than the other, this corresponding to the internal part of the tympanic canal facing towards the spiral ganglion, and which receives the said electrodes.

FIGS. 11 are diagrammatical cross-sections along the same plane as FIG. 10, of an electrode-carrier, in several configurations of shape and electrodes.

Figure 11A:
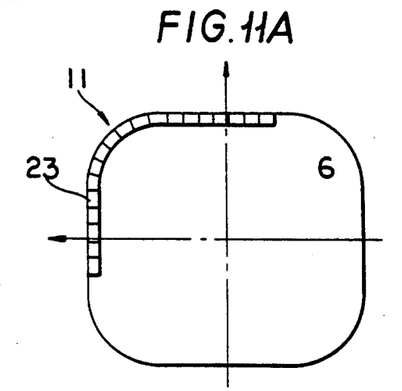
FIGS. 11A–11F are cross-sectional views of several configurations of designs and of electrodes.
Figure 11B:
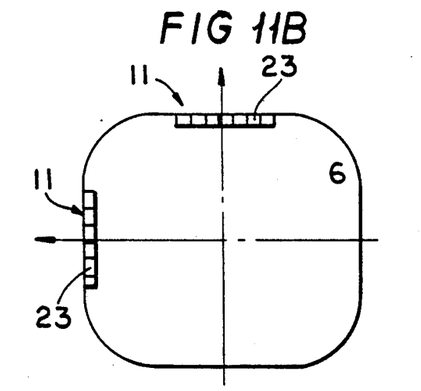
Figure 11C:
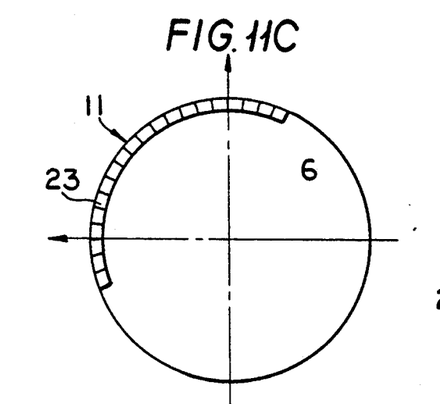
Figure 11D:
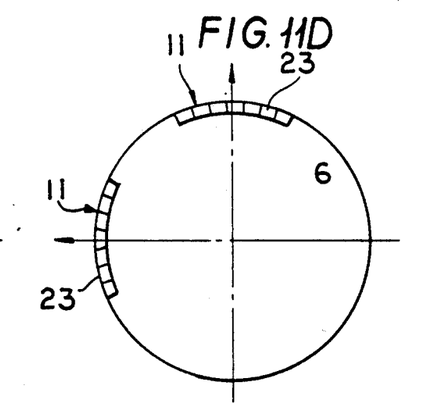
Figure 11E:
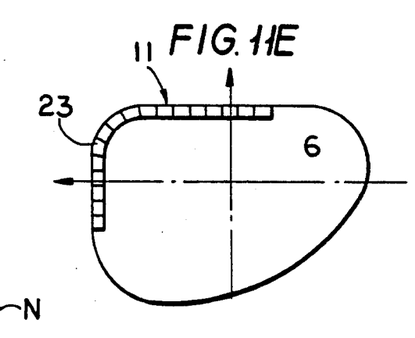
Figure 11F:
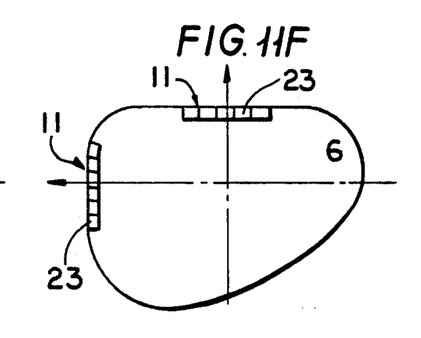

The sections of the body 6 in FIGS. 11A to 11D are all of symmetrical shape, either circular, or rectangular with rounded edges, and the sections according to FIGS. 11E and 11F are asymmetrical according to the definition and description of FIG. 10, where said sections are oval-shaped with the end or side receiving the electrodes being thicker than the other.

All the figures comprise electrodes whose active visible surfaces 23 are oriented substantially parallel towards the two sides of a solid angle defined on the one hand by the reference plane P already defined hereinabove and on the other hand, by a plane N which is substantially perpendicular to P and parallel to the two rotation axes CC' of the section carrying the electrodes 11 with respect to the two sections adjacent thereto: said plane N is in fact parallel to axis AA' of the cochlea and roughly tangential to the internal face 24 of the tympanic canal behind which is situated the spiral ganglion.

FIGS. 11A, 11C and 11E represent a configuration of a single electrode whose active face is continuous and adopts the sides of the body 6 corresponding to the sides of said solid angle facing it, as illustrated in FIG. 10.

FIGS. 11B, 11D and 11F represent a configuration of electrodes with a more limited active surface 23 directed towards only one of said sides of the solid angle N, P: it may be a single electrode of which two heads project from the body 6, or two independent electrodes optionally placed on two adjacent sections.

The present invention is not limited to the above-mentioned embodiments which are only examples for the production of electrode carrier devices according to the invention, and modifications and variants may be brought thereto without departing from its scope.

What is claimed is:

1. Intra-cochlear electrode carrier device for a tympanic helical shape canal implantation said helical shape curling around an osseous axis along AA', which also corresponds to that of the common section of the cochlear nervus acusticus, so as to electrically stimulate the latter, comprising a flexible support whose body has a surface and is made of biocompatible material in the shape of an elongated rod along its own axis BB', of substantially thick cross section with respect to its width and which can be laid substantially flat, when inoperative, in a reference plane P, substantially parallel to its own axis BB', which rod further comprises a base, a point on opposite ends and mechanical discontinuities defining and separating sections which are hinge-joined together and each section carrying at least one electrode having an active part with an active surface and connected via a conductor to a signal receiver included in the electrode device and generally placed at the back of the ear, said discontinuities forming hinges, of sufficient rigidity, the rotation axis of CC' of which are substantially perpendicular to said reference plane so that the sections can rotate substantially in parallel to said plane, and each said electrode is placed on its section with its active part directed towards the solid angle PN defined for its two sides, on the one hand, by said reference plane P and on the other hand, by a plane N substantially perpendicular to the plane P and substantially parallel to two rotation axes CC' of said electrode carrying section, with respect to the two sections adjacent thereto, in such a way that, when the electrode-carrier device is inserted in the cochlea, the flexible support spontaneously follows the curvature of the tympanic canal by rotation of the sections about the said rotation axis CC' which remains substantially parallel to the osseous axis AA' of the cochlea and which inevitably self-orientate the surface of the active part of the electrode towards the substantially nerveless zone to be stimulated.

2. Electrode carrier device as claimed in claim 1, wherein said mechanical discontinuities are transversal slits perpendicular to the flexible support's own axis BB' and which extend over a substantially large part of the cross sections thereof situated between two electrode sections, so that the hinges are non-split continuous portions of said cross sections.

3. Electrode carrier device as claimed in claim 1, wherein said mechanical discontinuities are veritable hinges with permanent contact points, whose articulation axes CC' are said rotation axes and which interconnect independent sections one to the other.

4. Electrode carrier device as claimed in claim 3, wherein said active part surfaces of the electrodes are visible on the surface of said body and are orientated towards the two sides of said solid angle PN, so that said surfaces, when inserted in the cochlea, can stimulate both the propria and the inside face of the tympanic canal behind which are situated the spiral ganglia.

5. Electrode carrier device as claimed in claim 4, wherein said electrodes have a continuous active surface which adopts the contour of said body along two sides thereof corresponding to those of said solid angle PN in facing relationship thereto.

6. Electrode carrier device as claimed in claim 4, wherein said electrodes comprise a tail which is embedded in the body of said support and which is shaped as a cross inside which are passed said conductors of connection between the signal receiver and said electrodes.

7. Electrode carrier device as claimed in claim 1, wherein said hinges are constituted on one side of a section by a cylindrical male part which engages on the other side in a corresponding female part of the adjacent section.

8. Electrode carrier device as claimed in claim 1, designed to be inserted in the cochlea of a right ear, in such a way that, all said electrodes are situated on a left side of the body of the flexible support when the latter is laid substantially flat, in inoperative position, in its reference plane P, with the face which, after insertion in the cochlea, must be orientated towards the propria of the cochlea, being orientated upwardly and, when looking at the base of the rod, towards the point which penetrates first into the cochlea.

9. Electrode carrier device as claimed in claim 1, designed to be inserted in the cochlea of a left ear in such a way that all said electrodes are situated on a right side of the body of the flexible support when the latter is laid substantially flat, in inoperative position, in its reference plane P with the face which, after the insertion in the cochlea must be orientated towards the propria of the cochlea, being orientated upwardly and when looking at the base of the rod, towards the point which penetrates first into the cochlea.

10. Electrode carrier device as claimed in claim 1, wherein all the sections of the body of the flexible support which are progressively reducing from the base towards the point, which penetrate first into the cochlea and which are substantially thick with respect to their width are approximately oval-shaped having two ends, one of the ends being thicker than the other, corresponding to the internal part of the tympanic canal facing towards the spiral ganglion and receiving said electrodes.

* * * * *